United States Patent
Witztum et al.

(10) Patent No.: US 8,883,428 B2
(45) Date of Patent: Nov. 11, 2014

(54) METHODS TO DETERMINE ATHEROSCLEROSIS REGRESSION, PLAQUE STABILIZATION AND CARDIOVASCULAR RISK

(75) Inventors: Joseph L. Witztum, San Diego, CA (US); Sotirios Tsimikas, San Diego, CA (US); Elizabeth Miller, Laguna Woods, CA (US)

(73) Assignee: The Regents of the University of California, Oakland, CA (US)

( * ) Notice: Subject to any disclaimer, the term of this patent is extended or adjusted under 35 U.S.C. 154(b) by 469 days.

(21) Appl. No.: 13/262,597

(22) PCT Filed: Apr. 2, 2010

(86) PCT No.: PCT/US2010/029769
§ 371 (c)(1),
(2), (4) Date: Sep. 30, 2011

(87) PCT Pub. No.: WO2010/115094
PCT Pub. Date: Oct. 7, 2010

(65) Prior Publication Data
US 2012/0035074 A1 Feb. 9, 2012

Related U.S. Application Data

(60) Provisional application No. 61/166,298, filed on Apr. 3, 2009.

(51) Int. Cl.
*G01N 33/53* (2006.01)
*G01N 33/68* (2006.01)
*G01N 33/92* (2006.01)
*C07K 16/18* (2006.01)

(52) U.S. Cl.
CPC ............ *C07K 16/18* (2013.01); *G01N 33/6893* (2013.01); *G01N 33/92* (2013.01); *G01N 2800/323* (2013.01); *G01N 2405/00* (2013.01); *G01N 2800/52* (2013.01)
USPC .......... 435/7.1; 435/7.92; 435/7.94; 436/501; 436/518

(58) Field of Classification Search
None
See application file for complete search history.

(56) References Cited

U.S. PATENT DOCUMENTS

2005/0095591 A1* 5/2005 Christopherson et al. ........ 435/6
2006/0177435 A1   8/2006 Tsimikas et al.

OTHER PUBLICATIONS

Penny et al., Improvement of Coronary Artery Endothelial Dysfunction With Lipid-Lowering Therapy: Heterogeneity of Segmental Response and Correlation With Plasma-Oxidized Low Density Lipoprotein, Journal of the American College of Cardiology, vol. 37, No. 3, 2001, pp. 766-774.*
Bergmark et al., A novel function of lipoprotein[a] as a preferential carrier of oxidized phopholipids in human plasma, Journal of Lipid Research, vol. 49, Jul. 2008, pp. 2230-2239.*
Edelstein et al., The oxidized phospholipids linked to human apolipoprotein(a) do not derive from circulating low-density lipoproteins and are probably of cellular origin, The FASEB Journal, vol. 23, Mar. 2009, pp. 950-956.*
Merki et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, Aug. 12, 2008, pp. 743-753, vol. 118.
Tsimikas et al., "Relationship of Oxidized Phospholipids on Apolipoprotein B-100 Particles to Race/Ethnicity, Apolipoprotein(a) Isoform Size, and Cardiovascular Risk Factors," Circulation, Mar. 23, 2009, pp. 1711-1719, vol. 119.
Kim, Yun-Kyung, International Search Report and Written Opinion, PCT/US2010/029769, Korean Intellectual Property Office, Jan. 20, 2011.

* cited by examiner

*Primary Examiner* — Gary W Counts
(74) *Attorney, Agent, or Firm* — Joseph R. Baker, Jr.; Gavrilovich, Dodd & Lindsey LLP

(57) ABSTRACT

Provided herein are compositions and methods for examining the progression, regression or risk of individuals at risk for developing coronary artery disease (CAD).

9 Claims, 3 Drawing Sheets

OxPL/apoA in ARBITER II

Change in OxPL/apoA with CETP Inhibitor

METHODS TO DETERMINE ATHEROSCLEROSIS REGRESSION, PLAQUE STABILIZATION AND CARDIOVASCULAR RISK

CROSS REFERENCE TO RELATED APPLICATIONS

This application is a U.S. National Stage filed under 35 U.S.C. §371 and claims priority to International Application No. PCT/US10/29769, filed Apr. 2, 2010, which application claims priority to U.S. Provisional Application Ser. No. 61/166,298, filed Apr. 3, 2009, the disclosures of which are incorporated herein by reference.

STATEMENTS REGARDING FEDERALLY SPONSORED RESEARCH

The invention was funded in part by Grant No. HL056989 awarded by National Institutes of Health (NIH). The government has certain rights in the invention.

TECHNICAL FIELD

Compositions and methods for identifying atherosclerosis regression, plaque stabilization and cardiovascular risk are provided.

BACKGROUND

The presence of chronic arterial inflammation in response to atherogenic stimuli has become a central tenet in explaining the development and destabilization of atherosclerotic plaques. Oxidized lipids play a central role in mediating a variety of immune, pro-inflammatory and plaque destabilizing processes that further amplify the inflammatory response.

SUMMARY

HDL and apolipoprotein A are involved in mediating reverse cholesterol transport. Currently, the method used to measure reverse cholesterol transport involves administering a radioactive compound to the patient and then measuring the label in lipoprotein and feces. This method is difficult, tedious and not amenable to large scale studies. The disclosure provides a high throughput method for measuring oxidized phospholipids on HDL and HDL-related lipoproteins, peptides or mimetics as a method for estimating reverse oxidized phospholipid transport or plaque stabilization. The assay utilizes an in vitro ELISA, has been optimized, and validated in rabbits, monkeys and humans.

The disclosure provides a method for quantifying the amount of phospholipids on HDL, apolipoprotein A and HDL or ApoA related particles. In one embodiment, a first antibody or binding fragment is coated on the bottom of a microtiter wall plate that can capture ApoA1 or other related HDL particles which may include ApoA1, apoA peptides, synthetic peptides such as apoA Milano peptides or 4Df and related apoA mimetics, as well as other lipoproteins that are on HDL particles such as apolipoprotein-E and apolipprotien-C2. Once the appropriate antibody or agent is placed on the bottom of a plate to capture these apoA or apoA-related particles, the plasma is added from a subject to be tested to capture the HDL-associated polypeptides. The content of oxidized phospholipids can be detected by suitable antibodies that measure oxidized phospholipids. One example is the monoclonal antibody EO6 and another example is DLH3, but other antibodies that bind oxidized phospholipids and not normal phospholipids can be used. The amount of antibody specific for oxPLs bound to HDL-associated polypeptides would reflect the amount of oxidized phospholipids present on the HDL (e.g., on an apoA polypeptide). The amount can be measured in a chemiluminescent ELISA or other similar assay.

The disclosure demonstrates the application of this technology to four different populations where one would expect to have effects on HDL content. The data demonstrated that when a therapeutic intervention is performed affecting apoA levels, there is an increase in the OxPL/apoA ratio suggesting that there is enrichment of the apoA particles in plasma with oxidized phospholipids consistent with a reverse cholesterol transport. The methods, compositions and kits of the disclosure are amenable to a laboratory testing product. Such methods and compositions are useful to measure the efficacy of drug therapies to treat atherosclerosis (such as, for example, the use of statins, niacins and the like). Such methods and compositions can also be useful in predicting cardiovascular risk or the increase in oxPL/apoA may by a marker of plaque stabilization or atherosclerosis regression.

The details of one or more embodiments of the disclosure are set forth in the accompanying drawings and the description below. Other features, objects, and advantages will be apparent from the description and drawings, and from the claims.

DETAILED DESCRIPTION

Figure 1:
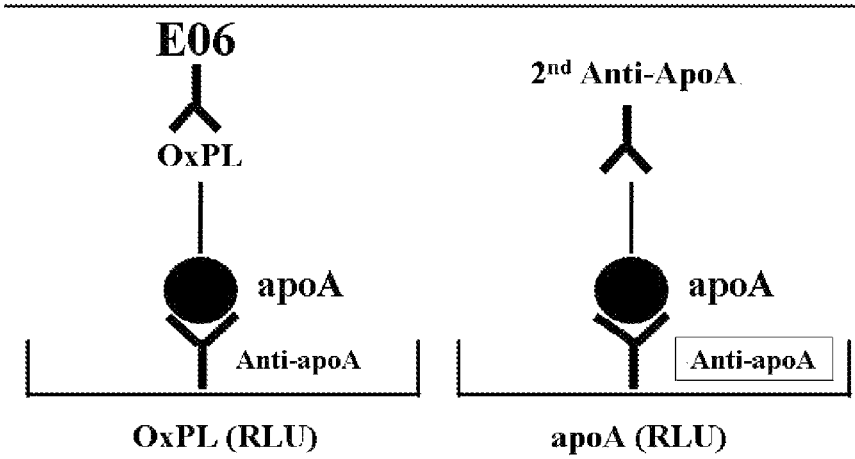
FIG. 1 shows a schematic of a method and composition of the disclosure.
Figure 2:
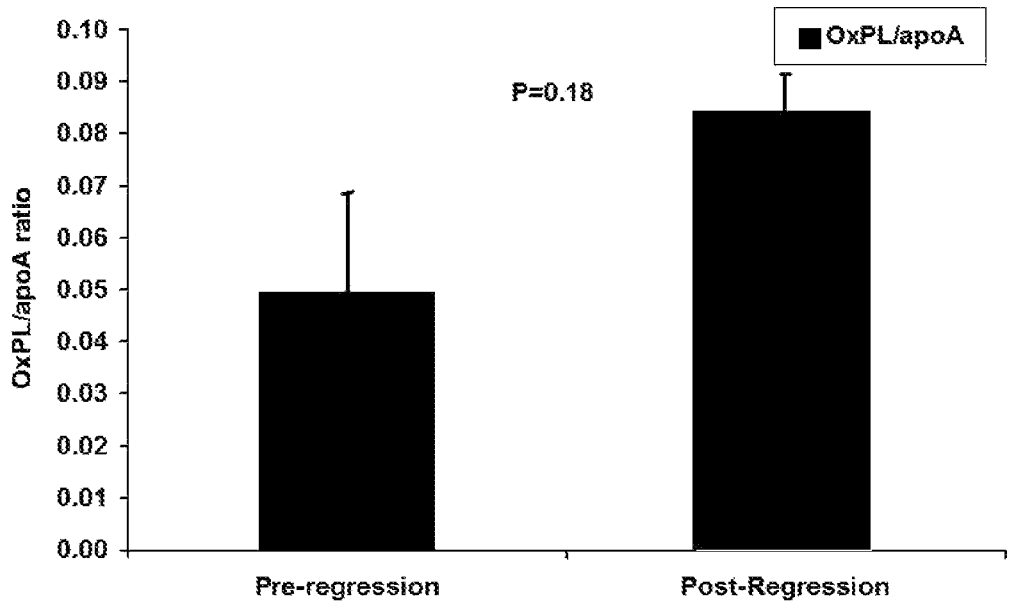
FIG. 2 shows measurements in cynomolgous monkeys using methods and compositions of the disclosure. An atherogenic diet was fed to cynomolgous monkeys (pre-regression), which then developed atherosclerosis. The atherogenic diet was then removed and the animals fed a low fat, low cholesterol diet. OxPL/apoA was then measured in the monkeys before and after the diet. A trend toward an increase in OxPL/apoA was noted.
Figure 3:
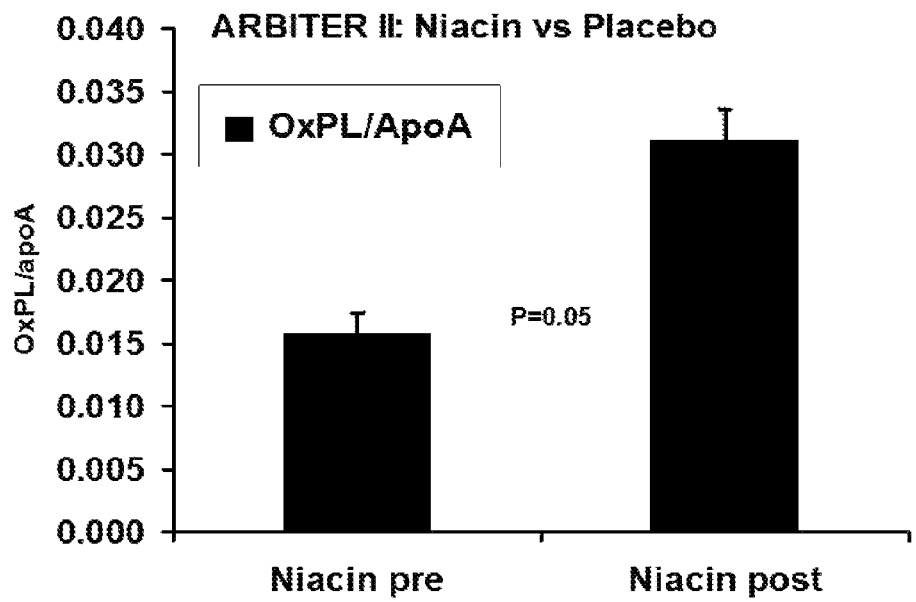
FIG. 3 shows a study of treated patients with coronary artery disease already on statins with niacin or placebo. OxPL/apoA was then measured before and after the treatment. The OxPL/apoA increased significantly following treatment with niacin.
Figure 4:
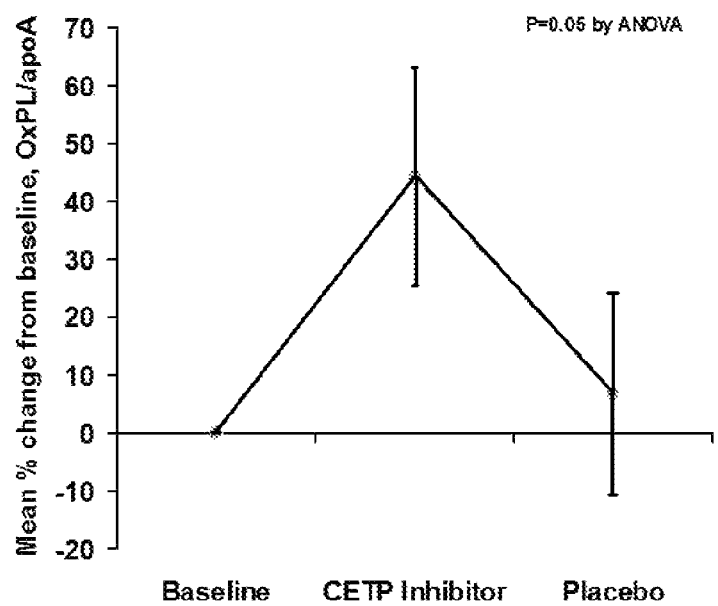
FIG. 4 shows the results of nineteen patients treated with JTT-705, a CETP inhibitor that induces increased HDL levels, presumably through reverse cholesterol transport. Patients were then taken off the JTT-705 and placed on placebo. The OxPL/apoA increased during the active treatment and decreased when placebo was instituted.
Figure 5:
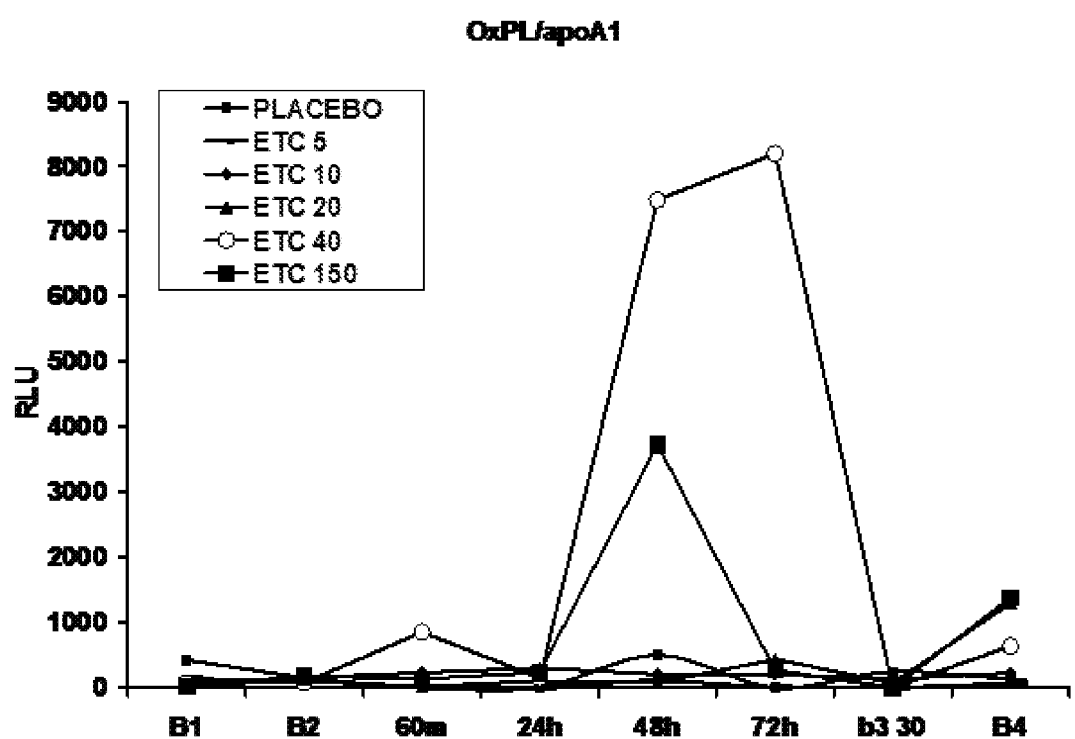
FIG. 5 shows lipid-rich plaque formation was induced in male New Zealand white rabbits. Rabbits were randomized into 6 groups of 6 animals each and treated with vehicle (7.7% sucrose and 0.8% mannitol) or 5, 10, 20, 40, 150 mg protein/Kg body weight of ETC-216 (ApoA Milano) administered as an intra-jugular infusion, at a constant rate of 1.0 mL/min, every 4 days, for a total of five doses. The data show significant increases in OxPL/apoA1 in the 2 groups of rabbits receiving the highest doses of ETC-216.

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

As used in this specification and the appended claims, the singular forms "a," "an," and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

All publications mentioned herein are incorporated herein by reference in full for the purpose of describing and disclosing the methodologies, which are described in the publications, which might be used in connection with the description herein. The publications discussed above and throughout the text are provided solely for their disclosure prior to the filing date of the present application. Nothing herein is to be construed as an admission that the inventors are not entitled to antedate such disclosure by virtue of prior disclosure.

Coronary artery disease (CAD) (also known as arteriosclerotic heart disease (AHD) of cardiac heart disease (CHD) is the narrowing or blockage of the coronary arteries caused by atherosclerosis. Atherosclerosis (sometimes called "hardening" or "clogging" of the arteries) is the buildup of cholesterol and fatty deposits (called plaque) on the inner walls of the arteries that restricts blood flow to the heart. Acute Coronary Syndrome is a name given to three types of coronary artery disease that are associated with sudden rupture of plaque inside the coronary artery: unstable angina, Non-ST segment elevation myocardial infarction or heart attack (NSTEMI), or ST segment elevation myocardial infarction or heart attack (STEMI). The length of time that blood flow is blocked and the amount of damage that occurs determines the type of acute coronary syndrome. An acute coronary syndrome can be caused by a small plaque, not necessarily detected by stress testing or cardiac catheterization. Prior symptoms may or may not be present.

For many years, epidemiologic studies have indicated that an individual's genetic composition is a significant risk factor for development of a vascular disease. For example, a family history of heart disease is associated with an increased individual risk of developing coronary artery disease. Lipid and cholesterol metabolism have historically been considered the primary genetic influence on coronary artery disease. For example, deficiency in cell receptors for low-density lipids (LDL), such as in familial hypercholesterolemia, is associated with high levels of plasma LDL and premature development of atherosclerosis (Brown & Goldstein, Sci., 191 (4223):150-4 (1976)).

A key problem in treating vascular diseases is proper diagnosis. Often the first sign of the disease is sudden death. For example, approximately half of all individuals who die of coronary artery disease die suddenly, Furthermore, for 40-60% of the patients who are eventually diagnosed as having coronary artery disease, myocardial infarction is the first presentation of the disease. Unfortunately, approximately 40% of those initial events go unnoticed by the patient.

Inflammation is now generally regarded as an important component of the pathogenic process of atherosclerosis (Munro, Lab Invest., 58:249-261 (1988); Badimon, et al., Circulation, 87:3-16 (1993); Liuzzo, et al., N.E.J.M., 331(7):417-24 (1994); Alexander, N.E.J.M., 331(7):468-9 (1994)). Several inflammatory products, including IL-1 beta, have been identified in atherosclerotic lesions or in the endothelium of diseased coronary arteries (Galea, et al., Ath. Thromb. Vasc. Biol., 16:1000-6 (1996)). Also, serum concentrations of IL-1 beta have been found to be elevated in patients with coronary disease (Hasdai, et al., Heart, 76:24-8 (1996)).

Oxidized phospholipids (OxPL) are pro-inflammatory and are detected by monoclonal antibody E06 on apolipoprotein B-100 particles (OxPL/apoB), and primarily on Lp(a) lipoprotein [Lp(a)].

Lp(a) is associated with enhanced atherogenic potential, particularly at levels >30 mg/dl, and has generally been shown to be an independent predictor (odds ratio ~1.5-2) of cardiovascular risk, particularly in younger subjects (<60 years old) and those with elevated LDL cholesterol levels. Since it appears that the atherogenicity of Lp(a) may be mediated in part by its association with OxPL. Cells loaded with cholesterol ester in the arteries cause the characteristic 'fatty streak' associated with the early stages of atherosclerosis.

The disclosure provides an in vitro assay that quantitates the amount of phospholipid on HDL, apolipoprotein A and HDL or ApoA related particles. Oxidized phospholipids are pro-inflammatory and pro-atherogenic and HDLs or its lipoprotein called apolipoprotein-A is involved in mediating reverse cholesterol transport, where it removes these oxidized phospholipids from the vessel wall to the liver for clearance. The disclosure provides a high throughput assay that will measure oxidized phospholipids on HDL and HDL-related lipoproteins, peptides or mimetics to measure reverse oxidized phospholipid transport, plaque stabilization or atherosclerotic risk regression.

The disclosure relates to the analysis of OxPL of patients at high risk, suspected to be at risk for or under treatment for a cardiovascular disease associated with high cholesterol or LDL levels. The methods and compositions of the disclosure are useful for diagnostic purposes and for monitoring the effects of dietary interventions, as well as for monitoring treatment for reducing cholesterol and high LDL levels using drugs such as statins. More particularly, the disclosure relates to methods and compositions useful for determining OxPL/apoA ratios as indices of atherosclerosis regression, reverse cholesterol metabolism and plaque stability.

In one embodiment, a method of determining whether a therapy is effective for treating coronary artery disease is provided. The method includes obtaining a first sample comprising plasma from a subject; administering a therapy to the subject; obtaining a second sample from the subject following administration of the therapy; determining the level of oxidized phospholipid (OxPL) bound to Apolipoprotein A (apoA) in the first sample and second sample; determining the level of total apoA in the first sample and the second sample; and calculating the ratio of the OxPL level to the apoA level for both samples. An increase in the ratio determined from the second sample in comparison to the ratio determined for the first sample, is indicative of an effective therapy for coronary artery disease and/or a reversal of cholesterol transport. The information may be provided to a caregiver.

In some embodiments, the level of OxPL and the level of apoA in the samples obtained from the subject are measured with two or more different biomolecules. The first biomolecule specifically interacts with OxPL and the second biomolecule specifically interacts with apoA. In some embodiments, the biomolecules are antibodies, such as, for example, monoclonal antibodies. The antibody that interacts with OxPL may be, for example, E06 or DLH3.

In one embodiment, the disclosure relates to a method for measuring the plasma content of oxidized phospholipids on apolipoprotein A particles (OxPL/apoA). For example, the content of OxPL and apoA may be measured with monoclonal antibodies that are specific for each of these OxPL constituents.

An exemplary biochemical test for identifying specific proteins, such as OxPL and apoA, employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). It is understood that commercial assay enzyme-linked immunosorbant assay (ELISA) kits for various plasma constituents are available.

In another embodiment, an OxPL/apoA index is further correlated with, the age of the subject at the time the ratios are measured, the subject's gender, and/or the subject's race.

In another embodiment, an article of manufacture is provided. The article may include packaging material containing biomolecules that interact with oxidized phospholipid (OxPL) and apoA. The packaging material may include a label or package insert indicating that the biomolecules can be used for calculating a regression index by determining the ratio of the OxPL level to the apoA level.

In yet another embodiment, an array is provided. The array may include a substrate having a plurality of addresses, each address having disposed thereon a set of one or more biomolecules that specifically interact with oxidized phospholipid (OxPL) or apoA.

The methods of the disclosure can be used with an array (i.e., "biochip" or "microarray") that includes immobilized biomolecules that facilitate the detection of a particular molecule or molecules in a biological sample. Biomolecules that identify the biomarkers described above can be included in a custom array for detecting OxPL or apoA. The array can also include biomolecules that identify additional factors indicative of the efficacy of a treatment for CAD. Additional biomolecules can be included in a custom array of the disclosure.

The term "array," as used herein, generally refers to a predetermined spatial arrangement of binding islands, biomolecules, or spatial arrangements of binding islands or biomolecules. Arrays according to the disclosure that include biomolecules immobilized on a surface may also be referred to as "biomolecule arrays." Arrays according to the disclosure that comprise surfaces activated, adapted, prepared, or modified to facilitate the binding of biomolecules to the surface may also be referred to as "binding arrays." The disclosure also contemplates surfaces bearing multiple arrays, referred to as "multiple arrays" or "repeating arrays." The use of the term "array" herein may encompass biomolecule arrays, binding arrays, multiple arrays, and any combination thereof, the appropriate meaning will be apparent from context. The biological sample can include fluid or solid samples from any tissue of the body including plasma.

An array of the disclosure or a solid phase comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from serum.

A planar array of the disclosure will generally contain addressable locations (e.g., "pads", "addresses," or "microlocations") of biomolecules in an array format. The size of the array will depend on the composition and end use of the array. Arrays containing from about 2 different biomolecules to many thousands can be made. In some embodiments, the compositions of the disclosure may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates. Parallel microfluidic devices comprising arrays would be useful for parallel measurements of OxPL and total ApoA content of a biological sample.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with a fluorescence based reporter system. Biomarkers can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems serum components can be simultaneously quantified from biological samples. An advantage of bead-based systems is the individual coupling of the capture biomolecule to distinct microspheres.

An array of the disclosure encompasses any means for detecting a biomarker molecule such as, for example, apoA and OxPL. For example, microarrays can be biochips that provide high-density immobilized arrays of recognition molecules (e.g., antibodies), where biomarker binding is monitored indirectly (e.g., via fluorescence). In addition, an array can be of a format that involves the capture of proteins by biochemical or intermolecular interaction, coupled with direct detection by mass spectrometry (MS).

Arrays and microarrays that can be used with the new methods to detect the biomarkers described herein can be made according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. New arrays, to detect specific selections of sets of biomarkers described herein can also be made using the methods described in these patents.

Surfaces useful according to the disclosure may be of any desired shape (form) and size. Non-limiting examples of surfaces include chips, continuous surfaces, curved surfaces, flexible surfaces, films, plates, sheets, tubes, and the like. Surfaces have areas ranging from approximately a square micron to approximately 500 $cm^2$. The area, length, and width of surfaces according to the disclosure may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

In another embodiment, a pre-packaged diagnostic kit for determining whether a therapy is effective for treating coronary artery disease is provided. The kit may include an array as described above, instructions for using the array, and instructions for calculating a regression index by determining the ratio of the OxPL level to the apoA level (e.g., total apoA).

Arrays of the disclosure suitable for identifying coronary artery disease, and the efficacy of a treatment therefore, may be included in kits. Such kits may also include, as non-limiting examples, reagents useful for preparing biomolecules for immobilization onto binding islands or areas of an array, reagents useful for detecting modifications to immobilized biomolecules, or reagents useful for detecting binding of biomolecules from solutions of interest to immobilized biomolecules, and instructions for use. Likewise, arrays comprising immobilized biomolecules may be included in kits. Such kits may also include, as non-limiting examples, reagents useful for detecting modifications to immobilized biomolecules or for detecting binding of biomolecules from solutions of interest to immobilized biomolecules.

In other embodiments, a method for identifying plaque regression, reverse cholesterol transport or stabilization in a blood vessel in a subject, is provided. The method includes obtaining a first sample comprising plasma from a subject; administering a therapy to the subject; obtaining a second sample from the subject following administration of the therapy; determining the level of oxidized phospholipid (OxPL) in the first sample and second sample; determining the level of apoA in the first sample and the second sample; calculating a regression index by determining the ratio of the OxPL level to the apoA level for both samples. An increase in the ratio determined from the second sample in comparison to the ration determined for the first sample, is indicative of an effective therapy, reversal of cholesterol transport for coronary artery disease. The information may be provided to a caregiver in various means including directly, paper print-out over, computer screen or over the internet to a remote location.

In yet another embodiment, a method for determining the phospholipid content of an apoA particle, is provided. The method includes obtaining a sample comprising apoA; determining the level of oxidized phospholipid (OxPL) in the sample; determining the level of apoA in the sample; and calculating an index by determining the ratio of the OxPL level to the apoA level.

The methods and compositions of the disclosure also provide a method of optimizing the treatment of a subject having or at risk of having a cardiovascular disease or disorder. The disclosure provides an approach to treating such a disorder by integrating diagnostics and therapeutics to improve the real-time treatment of a subject having, for example, a cardiovascular disease or disorder associated with cholesterol, HDL, or LDL content. For example, multiparameter immunoassays specific for a series of diagnostically relevant molecules such as OxPL, apoA, or apoB can be used to follow the progress of a subject undergoing treatment. The markers provided herein are particularly adaptable for use in diagnosis and treatment because they are available in easily obtained body fluids such as blood or serum.

In one embodiment, the disclosure provides an ELISA assay that can be used to measure reverse oxidized phospholipid transport.

In one embodiment, the assay format comprises the capture of intact lipoprotein A species. Antibody or antibody fragments that bind to an apolipoprotein A or antigen of apolipoprotein A (e.g., an apolipoprotein A binding agent) can be used in the assay. The binding agent can be linked to a solid phase or support (e.g., a bead, tissue culture plate, glass slide or the like. The agent is bound to the solid phase either by adsorption thereon or by covalent attachment. This binding agent can be an antibody such as those commercially available from The Binding Site, Birmingham, England, but it may also be another agent having specificity for the apolipoprotein.

The test is most conveniently carried out in multiwall microtiter plates, such as NUNC IMMUNOWELLS, (Irvine Scientific, Santa Ana, Calif.), but may also be performed in other solid phase media. The isolation of classes of intact lipoproteins should not be limited to techniques using only antibodies as binding agents. In the future, it is to be expected that other agents will be developed which specifically bind to apolipoprotein A polypeptides, peptides or antigens.

In one embodiment, the solid phase is coated with an antibody (or other binding agent) that interacts with an apolipoprotein A, such as for example apo AI and AII associated with HDL. Apolipoprotein A's are then separated from a sample of a specimen, such as for example, bodily fluids, tissue or cells, by allowing the lipoproteins to be bound thereto. The specimen may be any biological material containing lipoproteins, such as plasma or lymphatic fluid, or it may be the fluid portion of cells, such as those of the liver. The sample may be the crude specimen, or it may be a separated fraction, for example, a lipoprotein enriched sample, or a sample of an isolated lipoprotein class. The optimum time necessary for lipoprotein to bind quantitatively to the support can be determined empirically, by sequential trials.

After the lipoproteins are bound to the support, unbound lipoproteins are removed by rinsing with a buffer solution. Sites of the support which are available to non-specific binding may be blocked by treatment with a solution containing a protein such as for example albumin or gelatin.

To determine "total" apolipoprotein A in a sample a secondary antibody that specifically binds apolipoprotein is added to the solid support/phase and allowed to incubate for a period of time sufficient to allow the secondary antibody to interact with an antigenic site on the apolipoprotein A bound to the solid substrate/phase. The secondary antibody may be detectably labeled such that suitable quantitation of the apolipoprotein A may be determined. Suitable labels include fluorescent labels, luminescent labels, radioactive labels, chromogenic labels and the like. Unbound antibody can then be removed from the sample by washing.

A sample run in parallel or from the same biological sample is also measured for the presence of oxPL on the bound apolipoprotein A. OxPL can be determined by using an antibody that interacts with the oxidized phospholipid. Such antibodies are known in the art and includes the antibody designated E06.

The label attached to the probing antibodies may be an enzyme, such as peroxidase, alkaline phosphatase, or beta-galactosidase, as are commonly used in ELISA assays. These enzymes react with appropriate substrates to produce a colored compound, the concentration of which can be measured by its absorbance. In one embodiment of the test, however, the interaction of alkaline phosphatase or beta-galactosidase with a substrate methylumbelliferonyl phosphate generates a fluorescent product, detected by the same automated system used to measure the Nile Red binding.

Chemiluminescent enzyme-linked immunosorbent assay can be used also in apolipoprotein quantification. When the tagging enzyme is peroxidase, the detection system is Luminol/$H_2O_2$ (Stevens, P. et al., Lab Res. Methods Biol. Med. 4:205 (1980) The amount of light produced in these reactions is quantified using appropriate light measuring devices such as ML 1000 microplate luminometer (Dynatech Lab, Inc., 14340 Sully Field Circle, Chantilly, Va. 22021). Typically, when either fluorescent or chemiluminescent signals are to be read, the test is carried out on black plates.

In other embodiments, the disclosure provides databases and computerized methods of analyzing and storing data associated with treatment regimens for atherosclerosis related diseases. A database generated by the methods and analyses described herein can be included in, or associated with, a computer system for determining whether a treatment is successful. The database can include a plurality of digitally encoded "reference" (or "control") profiles. Each reference profile of the plurality can have a plurality of values, each value representing a level of, for example, OxPL or apoA detected in blood or serum of an individual having, or predisposed to having, an atherosclerosis related disorder. Alternatively, a reference profile can be derived from an individual who is normal. Both types of profiles can be included in the database for consecutive or simultaneous comparison to a subject profile. The computer system can include a server containing a computer-executable code for receiving a profile and identifying from the database a matching reference profile that is diagnostically relevant to the subject profile. The identified profile can be supplied to a caregiver for diagnosis or further analysis.

Using standard programs, electronic medical records (EMR) can be accumulated to provide a database that combines, for example, index data with additional information such as the age of a patient or any other parameter useful for predicting whether or not a subject will or is responding to a treatment. Patient information can be randomly assigned a numerical identifier to maintain anonymity with testing laboratories and for security purposes. All data can be stored on a network that provides access to multiple users from various geographic locations.

Thus, the various techniques, methods, and aspects of the disclosure described herein can be implemented in part or in whole using computer-based systems and methods. Additionally, computer-based systems and methods can be used to augment or enhance the functionality described herein, increase the speed at which the functions can be performed, and provide additional features and aspects as a part of, or in addition to, those of the invention described herein.

Antibodies capable of interacting with apoA or OxPL are known in the art. For example, a monoclonal antibody, designated E06 has been described that binds specifically to the phosphorylcholine head group of oxidized but not native phospholipids. Accordingly, this antibody can be used to determine the level of oxidized phospholipids in complex with apoA molecules. This antibody can be adapted for use in any immunoassay. For example, chemiluminescent ELISA assays are described elsewhere herein. Additional antibodies have been described in the literature that can also bind OxPL, such as DLH3 (Itabe et al., J Lipid Res. 1996; 37:45-53).

As discussed herein, "OxPL-E06" or "OxPL/apoA" is a measure of the content of oxidized phospholipids (OxPL) per apoA particle (e.g., total apoA, apoA-I or apoA-11).

A "cardiovascular disease" is a cardiovascular disorder, as defined herein, characterized by clinical events including clinical symptoms and clinical signs. Clinical symptoms are those experiences reported by a patient that indicate to the clinician the presence of pathology. Clinical signs are those objective findings on physical or laboratory examination that indicate to the clinician the presence of pathology. "Cardiovascular disease" includes both "coronary artery disease" and "peripheral vascular disease." Clinical symptoms in cardiovascular disease include chest pain, shortness of breath, weakness, fainting spells, alterations in consciousness, extremity pain, paroxysmal nocturnal dyspnea, transient ischemic attacks and other such phenomena experienced by the patient. Clinical signs in cardiovascular disease include such findings as EKG abnormalities, altered peripheral pulses, arterial bruits, abnormal heart sounds, rales and wheezes, jugular venous distention, neurological alterations and other such findings discerned by the clinician. Clinical symptoms and clinical signs can combine in a cardiovascular disease such as a myocardial infarction (MI) or a stroke (also termed a "cerebrovascular accident" or "CVA"), where the patient will report certain phenomena (symptoms) and the clinician will perceive other phenomena (signs) all indicative of an underlying pathology. "Cardiovascular disease" includes those diseases related to the cardiovascular disorders of fragile plaque disorder, occlusive disorder and stenosis. For example, a cardiovascular disease resulting from a fragile plaque disorder, as that term is defined below, can be termed a "fragile plaque disease." Clinical events associated with fragile plaque disease include those signs and symptoms where the rupture of a fragile plaque with subsequent acute thrombosis or with distal embolization are hallmarks. Examples of fragile plaque disease include certain strokes and myocardial infarctions. As another example, a cardiovascular disease resulting from an occlusive disorder can be termed an "occlusive disease." Clinical events associated with occlusive disease include those signs and symptoms where the progressive occlusion of an artery affects the amount of circulation that reaches a target tissue. Progressive arterial occlusion may result in progressive ischemia that may ultimately progress to tissue death if the amount of circulation is insufficient to maintain the tissues. Signs and symptoms of occlusive disease include claudication, rest pain, angina, and gangrene, as well as physical and laboratory findings indicative of vessel stenosis and decreased distal perfusion. As yet another example, a cardiovascular disease resulting from restenosis can be termed an in-stent stenosis disease. In-stent stenosis disease includes the signs and symptoms resulting from the progressive blockage of an arterial stent that has been positioned as part of a procedure like a percutaneous transluminal angioplasty, where the presence of the stent is intended to help hold the vessel in its newly expanded configuration. The clinical events that accompany in-stent stenosis disease are those attributable to the restenosis of the reconstructed artery.

A "coronary artery disease" ("CAD") refers to a vascular disorder relating to the blockage of arteries serving the heart. Blockage can occur suddenly, by mechanisms such as plaque rupture or embolization. Blockage can occur progressively, with narrowing of the artery via myointimal hyperplasia and plaque formation. Those clinical signs and symptoms resulting from the blockage of arteries serving the heart are manifestations of coronary artery disease. Manifestations of coronary artery disease include angina, ischemia, myocardial infarction, cardiomyopathy, congestive heart failure, arrhythmias and aneurysm formation. It is understood that fragile plaque disease in the coronary circulation is associated with arterial thrombosis or distal embolization that manifests itself as a myocardial infarction. It is understood that occlusive disease in the coronary circulation is associated with arterial stenosis accompanied by anginal symptoms, a condition commonly treated with pharmacological interventions and with angioplasty.

A "cardiovascular disorder" refers broadly to both coronary artery disorders and peripheral arterial disorders. The term "cardiovascular disorder" can apply to any abnormality of an artery, whether structural, histological, biochemical or any other abnormality. This term includes those disorders characterized by fragile plaque (termed herein "fragile plaque disorders"), those disorders characterized by vaso-occlusion (termed herein "occlusive disorders"), and those disorders characterized by restenosis. A "cardiovascular disorder" can occur in an artery primarily, that is, prior to any medical or surgical intervention. Primary cardiovascular disorders include, among others, atherosclerosis, arterial occlusion, aneurysm formation and thrombosis. A "cardiovascular disorder" can occur in an artery secondarily, that is, following a medical or surgical intervention. Secondary cardiovascular disorders include, among others, post-traumatic aneurysm formation, restenosis, and post-operative graft occlusion.

As used herein, the term "high density lipoprotein" or "HDL, or a subfraction thereof" includes protein or lipoprotein complexes with a density from about 1.06 to about 1.21 g/mL, or from about 1.06 to 1.10 g/mL, or from about 1.10 to about 1.21 g/mL, or a complex containing ApoA-I or ApoA-II. HDL may be prepared by density ultracentrifugation, as described in Mendez, A. J., et al., J. Biol. Chem. 266:10104-10111, 1991, from plasma, serum, bodily fluids, or tissue. The $HDL_3$ subfraction in the density range of about 1.110 to about 1.210 g/mL, and the $HDL_2$ subfraction in the density range of about 1.06 to about 1.110 g/mL may be isolated from plasma, serum, bodily fluids, tissue or total HDL by sequential density ultracentrifugation, as described in Mendez, supra. HDL is known to contain two major proteins, Apolipoprotein A-I (ApoA-I) and Apolipoprotein A-II (ApoA-II); therefore, in some embodiments, the term "HDL, or a subfraction thereof" also includes an ApoA-I and/or an ApoA-II containing protein or lipoprotein complex.

As used herein, the term "HDL-associated" refers to any biological compounds that float in the density range of HDL (d=about 1.06 to about 1.21 g/mL), and/or molecules present in a complex containing ApoA-I and/or ApoA-II, including full-length proteins, and fragments thereof, including peptides, or lipid-protein complexes such as microparticles, in HDL isolated from any sample, including lesions, blood, urine, or tissue samples.

The term "interact" as used herein is meant to include detectable relationships or associations (e.g. biochemical interactions) between molecules, such as interactions between protein-protein, protein-lipid, protein-nucleic acid, and the like.

The term "marker" refers to a sequence or a biological factor in the genome or subject that is known to vary among individuals and can be associated with a particular disease or disease risk.

The term "propensity to disease," also "predisposition" or "susceptibility" to disease or any similar phrase, means that certain markers are associated with or predictive of a subject's incidence of developing a particular disease (herein, a cardiovascular disease). The biomarker (e.g., the presence of a particular ratio or level of phospholipid or apoprotein) are thus over-represented or underexpressed (depending upon the marker) in frequency in individuals with disease as compared to healthy individuals.

"Stenosis," as understood herein refers to a narrowing of an artery as seen in occlusive disorder or in restenosis. Stenosis can be accompanied by those symptoms reflecting a decrease in blood flow past the narrowed arterial segment, in which case the disorder giving rise to the stenosis is termed a disease (i.e., occlusive disease or restenosis disease). Stenosis can exist asymptomatically in a vessel, to be detected only by a diagnostic intervention such as an angiography or a vascular lab study. The term "restenosis" refers to any preocclusive lesion that develops following a reconstructive procedure in a diseased blood vessel. The term is not only applied to the recurrence of a pre-existing stenosis, but also to previously normal vessels such as vein grafts that become partially occluded following vascular bypass. Restenosis refers to any luminal narrowing that occurs following a therapeutic intervention directed to an artery. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis. Restenosis can occur as the result of any time of vascular reconstruction, whether in the coronary vasculature or in the periphery (Colbum and Moore (1998) Myointimal Hyperplasia pp. 690-709 in Vascular Surgery: A Comprehensive Review (Philadelphia: Saunders, 1998)). For example, studies have reported symptomatic restenosis rates of 30-50% following coronary angioplasties (see Berk and Harris (1995) Adv. Intern. Med. 40:455-501). After carotid endarterectomies, as a further example, 20% of patients studied had a luminal narrowing greater than 50% (Clagett et al. (1986) J. Vasc. Surg. 3:10-23). Yet another example of restenosis is seen in infrainguinal vascular bypasses, where 40-60% of prosthetic grafts and 20-40% of the vein grafts are occluded at three years (Dalman and Taylor (1990) Ann. Vasc. Surg. 3:109-312, Szilagyi et al. (1973) Ann. Surg. 178:232-246). Different degrees of symptomatology accompany preocclusive lesions in different anatomical locations, due to a combination of factors including the different calibers of the vessels involved, the extent of residual disease and local hemodynamics. In-stent stenosis is a type of restenosis.

A "risk factor" is a factor identified to be associated with an increased risk. A risk factor for a cardiovascular disorder or a cardiovascular disease is any factor identified to be associated with an increased risk of developing those conditions or of worsening those conditions. A risk factor can also be associated with an increased risk of an adverse clinical event or an adverse clinical outcome in a patient with a cardiovascular disorder. Risk factors for cardiovascular disease include smoking, adverse lipid profiles, elevated lipids or cholesterol, diabetes, hypertension, hypercoagulable states, elevated homocysteine levels, and lack of exercise. Carrying a particular polymorphic allele is a risk factor for a particular cardiovascular disorder, and is associated with an increased risk of the particular disorder.

The term "treating" as used herein is intended to encompass curing as well as ameliorating at least one symptom of a disease or at least one abnormality associated with a disorder. Treating a cardiovascular disorder can take place by administering a cardiovascular disorder therapeutic. Treating a cardiovascular disorder can also take place by modifying risk factors that are related to the cardiovascular disorder.

A "treatment plan" refers to at least one intervention undertaken to modify the effect of a risk factor upon a patient. A treatment plan for a cardiovascular disorder or disease can address those risk factors that pertain to cardiovascular disorders or diseases. A treatment plan can include an intervention that focuses on changing patient behavior, such as stopping smoking. A treatment plan can include an intervention whereby a therapeutic agent is administered to a patient. As examples, cholesterol levels can be lowered with proper medication, and diabetes can be controlled with insulin. Nicotine addiction can be treated by withdrawal medications. A treatment plan can include an intervention that is diagnostic. The presence of the risk factor of hypertension, for example, can give rise to a diagnostic intervention whereby the etiology of the hypertension is determined. After the reason for the hypertension is identified, further treatments may be administered.

The invention is illustrated in the following examples, which are provided by way of illustration and are not intended to be limiting.

EXAMPLES

Reagents: Tris buffered saline (TBS buffer): for 20 liters (10× concentrate) 1753 gm NaCl, 1212 gm Tris Base, 20 gm EDTA (final conc. of 0.27 mM) 40 gm sodium azide (final conc. of 0.02%) HCl to pH 7.4 (approx. 750 ml). DILUTION BUFFER: 5 gm BSA (1% BSA) (RIA grade, SIGMA 100 gm A-7888), in 500 ml TBS buffer (containing 0.02% azide and 20 μM BHT). WASH BUFFER: TBS buffer. ACTIVATORS: 20 mM MgCl2 (1.904 gm/L), 20 mM ZnCL2 (2.726 gm/L), 0.4% azide (4 gm/L). PLATES: Dynex Microfluor white U-bottom, 96 wells.

Determine amount of OxPL on apoA1: Add an apo A-1 capture antibody such as Sheep anti-Human Apolipoprotein A-1 (The Binding Site, Birmingham, England) at 5-10 μg/ml to TBS buffer (or PBS) for overnight incubation at 4° C. Add 50 μl/well. The next day, wash plates with an automatic plate washer, 3 times 200 μl/well. Postcoat wells with 1% BSA/TBS@100 μl/well, 30-45 min, then wash before adding plasma. Add 50 μl plasma diluted to 1:50 in the appropriate well. For row "H" use 50 μl 1% BSA in TBS (Dilution buffer) as the blank. Leave at room temperature for 1-2 hours. Wash plate as above. Dilute the secondary antibody (biotinylated E06@1 μg/ml) and add 50 μl/well. After 1 hr at room temperature, wash plates as above. Prepare alkaline phosphatase labeled neutrAvidin (for biotin antibodies) or alkaline phosphatase labeled goat anti-rabbit IgG diluted in buffer containing activators (at 1:20 dilution. The activators keep the alkaline phosphatase antibodies consistent for months.) Add 50 μl to each well. Incubate at room temperature for 1 hour. Wash plate with cell washer set at 4 washes. Add 25 μl of detector for alkaline phosphatase, such as Lumi-phos 530 (keep sterile) diluted 1:1 in dist. water. Then leave at room temp. for 1.5-2 hr. Keep in the dark. Read in Chemiluminescence detector as relative light units (RLU). All assays are run in triplicate.

Determine amount of ApoA1 captured on the plate: Step 1: same as above. Step 2: same as above, except use rabbit anti-human apoA-1 at 5 μg/ml instead of E06. Determine OxPL/apoA1 Ratio (see FIG. 1): Divide OxPL RLU by apoA1 RLU.

Determine OxPL on all apoA Particles, i.e. Total OxPL-apoA:

Multiple OxPL/apoA1ratio with plasma levels of apoA determined with an independent technique.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining whether a therapy is effective for promoting reverse cholesterol transport, the method comprising:
   contacting a substrate comprising an antibody that binds apoA, wherein the antibody is linked to the substrate, with a sample from a subject under conditions wherein apoA in the sample is bound by the antibody;
   washing the substrate;
   contacting the bound apoA with a detectably labeled antibody that specifically binds to OxPL;
   obtaining optical data from the detectable label with a CCD camera;
   quantifying the amount of OxPL from the optical data; and
   calculating the OxPL bound to apoA before and after a therapy in the subject, wherein an increase in the OxPL after therapy is indicative of an effective therapy that promotes reverse cholesterol transport.

2. The method of claim 1, wherein the method quantitates an OxPL:ApoA ratio comprising OxPL bound to ApoA.

3. The method of claim 2, wherein an ApoA value of the OxPL:ApoA ratio comprises total ApoA.

4. The method of claim 1, wherein the antibody that binds OxPL is E06 or DLH3.

5. The method of claim 1, wherein the antibodies are monoclonal antibodies.

6. The method of claim 1, wherein the antibody on the substrate is immobilized to form an array.

7. The method of claim 6, wherein the array comprises a first set of a plurality of the first biomolecule and a second set of a plurality of the second biomolecule.

8. The method of claim 1, further comprising providing the determination to a caregiver.

9. The method of claim 1, wherein the subject is human.

* * * * *